United States Patent
Kawamura

(10) Patent No.: US 9,274,125 B2
(45) Date of Patent: Mar. 1, 2016

(54) METHOD AND KIT FOR MEASURING COMPONENT IN THE PRESENCE OF FATTY ACID ALKANOLAMIDE OR NONIONIC POLYOXYETHYLENE SURFACTANT

(75) Inventor: Mizuho Kawamura, Shizuoka (JP)

(73) Assignee: KYOWA MEDEX CO., LTD., Tokyo (JP)

( * ) Notice: Subject to any disclaimer, the term of this patent is extended or adjusted under 35 U.S.C. 154(b) by 0 days.

(21) Appl. No.: 13/501,318

(22) PCT Filed: Oct. 27, 2010

(86) PCT No.: PCT/JP2010/069027
§ 371 (c)(1),
(2), (4) Date: May 21, 2012

(87) PCT Pub. No.: WO2011/052620
PCT Pub. Date: May 5, 2011

(65) Prior Publication Data
US 2012/0219966 A1 Aug. 30, 2012

(30) Foreign Application Priority Data
Oct. 30, 2009 (JP) .................................. 2009-250639

(51) Int. Cl.
*G01N 33/53* (2006.01)
*G01N 33/566* (2006.01)
*A61K 39/385* (2006.01)
*G01N 33/68* (2006.01)

(52) U.S. Cl.
CPC .................................. *G01N 33/6866* (2013.01)

(58) Field of Classification Search
CPC ..... A61K 2300/00; A61K 8/86; G01N 21/75; G01N 33/5008; G01N 33/5023; G01N 33/585; G01N 33/6872
See application file for complete search history.

(56) References Cited

U.S. PATENT DOCUMENTS

| | | | | |
|---|---|---|---|---|
| 4,208,479 | A * | 6/1980 | Zuk et al. .................. | 435/7.9 |
| 5,352,583 | A | 10/1994 | Sakata et al. | |
| 8,043,822 | B2 * | 10/2011 | Kawamura et al. ............ | 435/7.1 |
| 2008/0118931 | A1 | 5/2008 | Murayama et al. | |
| 2012/0052591 | A1 | 3/2012 | Kawamura et al. | |

FOREIGN PATENT DOCUMENTS

| | | |
|---|---|---|
| CN | 101568834 | 10/2009 |
| EP | 0 318 081 | 5/1989 |
| EP | 0 450 086 | 10/1991 |
| EP | 0 725 081 | 8/1996 |
| EP | 2 085 782 | 8/2009 |
| EP | 2 098 864 | 9/2009 |
| JP | 62-000417 | 1/1987 |
| JP | H01-168624 | 7/1989 |
| JP | 05-312807 | 11/1993 |
| JP | 6-66798 | 3/1994 |
| JP | 2003-294752 | 10/2003 |
| JP | 2008-101924 | 5/2008 |
| JP | 2009-186359 | 8/2009 |
| WO | 91/05257 | 4/1991 |
| WO | 2006/073073 | 7/2006 |
| WO | 2008/053973 | 5/2008 |

OTHER PUBLICATIONS

Deisenhammer et al., (Neurology 1999;52:1239-1243) and JP 62-417A.*
Translated paragraph of JP62-417; 1987.*
Machine Translation of JP 6-99292 B (Equivalent of JP 62-417 A).*
2005 SPI catalog http://www.2spi.com/catalog/supp/triton-x-100.html).*
BASF catalog 2001-2011,URL:http://worldaccount.basf.com/wa/NAFTA~en_US/Catalog/ChemicalsNAFTA/pi/BASF/Brand/pluronic.*
Aebi, et al., "cDNA Structures and Regulation of Two Interferon-Induced Human Mx Proteins", Molecular and Cellular Biology, vol. 9, No. 11 (1989) 5062-72.
Haller, et al., "Interferon-Induced Mx Proteins: Dynamin-Like GTPases with Antiviral Activity", Traffic, vol. 3, No. 10 (2002) 710-17.
Horisberger, et al., "Cloning and Sequence Analyses of cDNAs for Interferon- and Virus-Induced Human Mx Proteins . . . ", Journal of Virology, vol. 64, No. 3 (1990) 1171-81.
Horisberger, et al., "IFN-α Induced Human 78 kD Protein: Purification and Homologies with the Mouse Mx Protein, Production of . . . ", Journal of Interferon Research, vol. 7, No. 4 (1987) 331-43.
Schumacher, et al., "Domains Mediating Intramolecular Folding and Oligomerization of MxA GTPase", Journal of Biological Chemistry, vol. 273, No. 43 (1998) 28365-70.
Vallittu et al., "MxA protein assay for optimal monitoring of IFN-β bioactivity in the treatment of MS patients", Acta Neurol Scand, vol. 118, No. 1 (2008) 12-17.
Wang, et al, Food Safety Inspecting Techniques, China Agricultural University Press 1st edition (2009) 321-2.
Wang, et al, The Chinese Dictionary of Laboratory Medicine, Shanghai Scientific and Technology Press, 1st edition (2010) 853-4.

* cited by examiner

*Primary Examiner* — Shafiqul Haq
*Assistant Examiner* — Carmencita M Belei
(74) *Attorney, Agent, or Firm* — Fitzpatrick, Cella, Harper & Scinto

(57) ABSTRACT

Methods and kits for measuring a component to be measured by reacting the component in the presence of a fatty acid alkanolamide, with a first antibody which binds to the component, then reacting a labeled second antibody that binds to the component so as to form an immunocomplex comprising the first antibody, the component and the labeled second antibody. The amount of the label in the formed immunocomplex is measured and correlated to the amount and concentration of component.

22 Claims, No Drawings

METHOD AND KIT FOR MEASURING COMPONENT IN THE PRESENCE OF FATTY ACID ALKANOLAMIDE OR NONIONIC POLYOXYETHYLENE SURFACTANT

This application is a National Phase of PCT Application No. PCT/JP2010/069027 filed Oct. 27, 2010, which in turn claims priority of Japanese Application No. 2009-250639 filed Oct. 30, 2009.

TECHNICAL FIELD

The present invention relates to methods and kits for measuring a component to be measured in a specimen.

BACKGROUND ART

Immunological measurement methods are being used as methods for measuring components in specimens. Immunological measurement methods include many methods such as the RIA method (radioimmunoassay), EIA method (enzyme immunoassay), CLIA method (chemiluminescent immunoassay), CLEIA (chemiluminescent enzyme immunoassay), LA method (latex agglutination method), TIA method (turbidimetric immunoassay), and immunochromatography method. In these assays, when the measurement is carried out by immunological techniques, the antigen-antibody reaction between a component (or antibody) in a specimen and an antibody (or antigen) against it is utilized. Furthermore, in these immunological assays, a calibration curve (standard curve) is made in advance by plotting onto a graph the relationship between numerical values (absorbances) obtained by measuring a standard material having known concentrations and their respective measured values (concentrations), and the measured values of the component of interest in the specimen is obtained. Recombinant antigens which can be prepared in large amounts and for which raw materials are readily available are commonly used for the standard material to be used in these assays.

However, the immunoreactivity of a recombinant antigen does not necessarily match that of the native antigen, which is the component in the specimen, and the reactivity may also differ depending on the buffer and additives used during the assay. In particular, when the reaction temperature during the antigen-antibody reaction changes, the difference in reactivity of the two become prominent, and this causes the problem of producing variations in measured values due to temperature (see Patent Documents 1 and 2).

MxA protein is a protein in the series of proteins induced by type I interferon (interferon α/β), has a molecular weight of 78 kDa, belongs to the Dynamin superfamily, has GTPase activity, and is expressed in the cytoplasm of leukocytes, particularly mononuclear cells. Regarding its function, it is known to have an antiviral effect due to inhibition of virus proliferation, and it is said to be involved in the establishment of antiviral conditions of an organism in the early stage of viral infection (see Non-Patent Documents 1 to 4).

The MxA protein found in several animal species has a characteristic amino acid sequence in its amino acid terminus. The N-terminal G domain is a part necessary for antiviral action and activity as GTPase, and the C-terminal region is abundant in α helical structures and has a leucine zipper structure. These two parts have been reported to react with each other intramolecularly, or cause self aggregation by binding with each other intermolecularly (see Non-Patent Document 5).

PRIOR ART DOCUMENTS

Patent Documents

[Patent Document 1] Japanese Patent Application Kokai Publication No. (JP-A) 2008-101924 (unexamined, published Japanese patent application)
[Patent Document 2] WO 2006/073073

Non-Patent Documents

[Non-Patent Document 1] J. Interferon Res., vol. 7, p. 331-343 (1987).
[Non-Patent Document 2] Mol. Cell. Biol., vol. 9, p. 5062-5072 (1989).
[Non-Patent Document 3] J. Virol., vol. 64, p. 1171-1181 (1990).
[Non-Patent Document 4] Traffic, vol. 3, p. 710-717 (2002).
[Non-Patent Document 5] J. Biological Chem., vol. 273, p. 28365-28370 (1998).

SUMMARY OF THE INVENTION

Problems to be Solved by the Invention

An objective of the present invention is to provide a method and a kit for measuring components to be measured in a specimen, whereby measurement of the components to be measured, such as antigens, in the specimen can be carried out accurately without being affected by the reaction temperature and so on.

Means for Solving the Problems

The present inventors carried out dedicated examinations to solve the problems and found that, in an immunoassay of a component to be measured in a specimen, accurate measurement becomes possible without being affected by the reaction temperature and so on by reacting, in the presence of a fatty acid alkanolamide, a component to be measured in a specimen with a first antibody that binds to the component to be measured. In addition, the present inventors found that, in an immunoassay of a component to be measured in a specimen, accurate measurement becomes possible without being affected by the reaction temperature and so on by reacting the component to be measured in the specimen with the first antibody which binds to the component to be measured, followed by reacting the component to be measured with, in the presence of a polyoxyethylene nonionic surfactant, a labeled second antibody, in which a label is bound to a second antibody that binds to the component to be measured; and the present inventors completed the present invention. More specifically, the present invention relates to [1] to [28] below:

[1] a method for measuring a component to be measured, wherein the method comprises reacting in the presence of a fatty acid alkanolamide, a component to be measured in a specimen with a first antibody which binds to the component to be measured; then reacting a labeled second antibody, in which a label is bound to a second antibody that binds to the component to be measured, to form an immunocomplex comprising the first antibody, the component to be measured, and the labeled second antibody; and measuring the amount of the label in the formed immunocomplex;

[2] the method of [1], wherein the labeled second antibody is reacted in the presence of a polyoxyethylene nonionic surfactant;

[3] a method for measuring a component to be measured, wherein the method comprises reacting a component to be measured in a specimen with a first antibody which binds to the component to be measured; then reacting in the presence of a polyoxyethylene nonionic surfactant, a labeled second antibody, in which a label is bound to a second antibody that binds to the component to be measured, to form an immunocomplex comprising the first antibody, the component to be measured, and the labeled second antibody; and measuring the amount of the label in the formed immunocomplex;

[4] the method of [1] or [2], wherein the fatty acid alkanolamide is fatty acid diethanolamide;

[5] the method of [2] or [3], wherein the polyoxyethylene nonionic surfactant is a polyoxyethylene nonionic surfactant selected from the group consisting of polyoxyethylene polyoxypropylene copolymer, polyoxyethylene polyoxypropylene alkyl ether, and ethylenediamine polyoxyethylene polyoxypropylene condensate;

[6] the method of [2], wherein the fatty acid alkanolamide is fatty acid diethanolamide, and the polyoxyethylene nonionic surfactant is a polyoxyethylene nonionic surfactant selected from the group consisting of polyoxyethylene polyoxypropylene copolymer, polyoxyethylene polyoxypropylene alkyl ether, and ethylenediamine polyoxyethylene polyoxypropylene condensate;

[7] the method of any one of [1] to [6], wherein a bile acid derivative is added and the component to be measured in a specimen is reacted with the first antibody that binds to the component to be measured;

[8] the method of [7], wherein the bile acid derivative is a bile acid derivative having zwitterionic surfactant action;

[9] the method of [8], wherein the bile acid derivative having zwitterionic surfactant action is 3-[(3-cholamidopropyl)dimethylammonio]propanesulfonate or 3-[(3-cholamidopropyl) dimethylammonio]-2-hydroxypropanesulfonate;

[10] the method of [7], wherein the bile acid derivative is a bile acid derivative having nonionic surfactant action;

[11] the method of [10], wherein the bile acid derivative having nonionic surfactant action is N,N-bis(3-gluconamidopropyl)cholamide or N,N-bis(3-D-gluconamidopropyl)deoxycholamide;

[12] the measurement method of any one of [1] to [11], wherein the first antibody is immobilized onto an insoluble carrier;

[13] the method of any one of [1] to [12], wherein the specimen is whole blood;

[14] the method of any one of [1] to [13], wherein the component to be measured is MxA protein;

[15] a kit for measuring a component to be measured in a specimen, wherein the kit comprises a first reagent comprising a first antibody which binds to a component to be measured and a fatty acid alkanolamide; and a second reagent comprising a labeled second antibody, in which a label is bound to a second antibody that binds to the component to be measured;

[16] the kit of [15], wherein the second reagent further comprises a polyoxyethylene nonionic surfactant;

[17] a kit for measuring a component to be measured in a specimen, wherein the kit comprises a first reagent comprising a first antibody which binds to a component to be measured; and a second reagent comprising a labeled second antibody, in which a label is bound to a second antibody that binds to the component to be measured, and a polyoxyethylene nonionic surfactant;

[18] the kit of [15] or [16], wherein the fatty acid alkanolamide is fatty acid diethanolamide;

[19] the kit of [16] or [17], wherein the polyoxyethylene nonionic surfactant is a polyoxyethylene nonionic surfactant selected from the group consisting of polyoxyethylene polyoxypropylene copolymer, polyoxyethylene polyoxypropylene alkyl ether, and ethylenediamine polyoxyethylene polyoxypropylene condensate;

[20] the kit of [16], wherein the fatty acid alkanolamide is fatty acid diethanolamide, and the polyoxyethylene nonionic surfactant is a polyoxyethylene nonionic surfactant selected from the group consisting of polyoxyethylene polyoxypropylene copolymer, polyoxyethylene polyoxypropylene alkyl ether, and ethylenediamine polyoxyethylene polyoxypropylene condensate;

[21] the kit of any one of [15] to [20], wherein the first reagent further comprises a bile acid derivative;

[22] the kit of [21], wherein the bile acid derivative is a bile acid derivative having zwitterionic surfactant action;

[23] the kit of [22], wherein the bile acid derivative having zwitterionic surfactant action is 3-[(3-cholamidopropyl)dimethylammonio]propanesulfonate or 3-[(3-cholamidopropyl) dimethylammonio]-2-hydroxypropanesulfonate;

[24] the kit of [21], wherein the bile acid derivative is a bile acid derivative having nonionic surfactant action;

[25] the kit of [24], wherein the bile acid derivative having nonionic surfactant action is N,N-bis(3-gluconamidepropyl) cholamide or N,N-bis(3-D-gluconamidepropyl)deoxycholamide;

[26] the kit of any one of [15] to [25], wherein the first antibody is immobilized onto an insoluble carrier;

[27] the kit of any one of [15] to [26], wherein the specimen is whole blood; and

[28] the kit of any one of [15] to [27], wherein the component to be measured is MxA protein.

Effects of the Invention

The present invention provides methods and kits for measuring components to be measured in a specimen, which allow accurate measurements with no influence of the reaction temperature and so on.

MODE FOR CARRYING OUT THE INVENTION (1) Specimen

The specimen to be used in the present invention is not particularly limited as long as it is a specimen that allows measurement by the present invention, and examples include whole blood (blood), blood cells, serum, plasma, spinal fluid, urine, tissues, and cultured cells. Whole blood includes specimens in which plasma is mixed with a blood cell fraction derived from whole blood. Whole blood may be blood collected from a subject as is, or it may be blood obtained after treating the collected blood, and treated blood is preferred. Examples of treatment include anticoagulation treatment and hemolysis treatment, and these treatments can be combined.

When the component (the object of measurement) is an intracellular component of a blood cell, blood subjected to hemolysis treatment is preferred as the whole blood, and blood subjected to both anticoagulation treatment and hemolysis treatment is particularly preferred. Examples of anticoagulation treatment include treatments in which EDTA, heparin, or such is added to the collected blood. Examples of hemolysis treatment include addition of a surfactant or saponin solution, mixing with a hypotonic solution, freeze-thawing, sonication, and such.

(2) Component to be Measured

The component to be measured in the present invention is not particularly limited so long as it is a component to be measured that enables measurement by the present invention, and examples include nucleic acids, proteins, lipids, vitamins, and polysaccharides. Examples of nucleic acids include DNA, RNA, ATP, ADP, AMP, and cyclic AMP. Examples of proteins include enzymes, hormones, and various peptides.

Suitable components to be measured in the present invention include substances contained in cells and metabolites, and are preferably proteins and such induced in cells by various cytokines such as interferons. A specific example of the component to be measured is the MxA protein which is induced in the cytoplasm by type I interferon (see the aforementioned Non-Patent Documents 2 to 3).

(3) Fatty Acid Alkanolamide

Examples of fatty acid alkanolamide of the present invention include fatty acid diethanolamide, fatty acid monoethanolamide, fatty acid N-methylethanolamide, fatty acid monoisopropanolamide, and fatty acid diisopropanolamide, and fatty acid diethanolamide is preferred. Examples of fatty acid diethanolamide include lauric acid diethanolamide, capric acid diethanolamide, caprylic acid diethanolamide, decanoic acid diethanolamide, myristic acid diethanolamide, palmitic acid diethanolamide, stearic acid diethanolamide, isostearic acid diethanolamide, oleic acid diethanolamide, linolic acid diethanolamide, octyldecanoic acid diethanolamide, coconut oil fatty acid diethanolamide, coconut fatty acid diethanolamide, beef tallow fatty acid diethanolamide, alkylalkanolamide, and palm kernel oil fatty acid diethanolamide. Among these, oleic acid diethanolamide, coconut fatty acid diethanolamide, and palm kernel oil fatty acid diethanolamide are preferred. Specific examples (commercially available products) of oleic acid diethanolamide include Stafoam DO and Stafoam DOS (the above are manufactured by NOF Corporation); specific examples (commercially available products) of coconut fatty acid diethanolamide include Stafoam F, Stafoam DFC, and Stafoam DF4 (the above are manufactured by NOF Corporation); and specific examples (commercially available products) of palm kernel oil fatty acid diethanolamide include Aminon PK-02S and Aminon PK-03S (the above are manufactured by Kao Corporation).

The concentration of a fatty acid alkanolamide in an antigen-antibody reaction is not particularly limited as long as it is a concentration that enables the measurement method of the present invention, and is, for example, 0.1% to 1.4%. In the present invention, fatty acid alkanolamide can be used alone (one kind), or in combination of two or more kinds.

(4) Polyoxyethylene Nonionic Surfactant

The polyoxyethylene nonionic surfactant in the present invention is not particularly limited as long as it enables the measurement method of the present invention, and examples include polyoxyethylene polyoxypropylene copolymer (hereinafter written as POE.POP copolymer), polyoxyethylene polyoxypropylene alkyl ether (hereinafter, written as POE.POP alkyl ether), polyoxyethylene polyoxypropylene alkylphenyl ether (hereinafter written as POE.POP alkylphenyl ether), polyoxyethylene polycyclic phenyl ether (hereinafter written as POE polycyclic phenyl ether), polyoxyethylene polyoxypropylene polycyclic phenyl ether (hereinafter written as POE.POP polycyclic phenyl ether), or ethylenediamine polyoxyethylene polyoxypropylene condensate (hereinafter written as ethylenediamine POE.POP condensate). POE.POP copolymer, POE.POP alkyl ether, and ethylenediamine POE.POP condensate are preferred, and POE.POP copolymer are particularly preferred.

The POE.POP copolymer may be block copolymer or random copolymer. Specific examples (commercially available products) of POE.POP copolymer include Pronon 102, Pronon 104, Pronon 201, Pronon 202B, Pronon 204, Pronon 208, Pronon 403 (the above are manufactured by NOF Corporation), Emulgen PP-230, Emulgen PP-250, Emulgen PP-290 (the above are manufactured by Kao Corporation), Pluronic L-101, Pluronic L-103, Pluronic L-121, Pluronic L-122, and Pluronic F-108 (the above are manufactured by Asahi Denka Co. Ltd.)

Specific examples (commercially available products) of POE.POP alkyl ether include Unilube 50 MB-168, Unilube 75DE-25, Unilube 75DE-3800, Unilube MT-0620B (the above are manufactured by NOF Corporation), Unisafe PKA-5015, Unisafe PKA-5016 (the above are manufactured by NOF Corporation), EMALEX DAPE-220, EMALEX DAPE-230 (the above are manufactured by Nihon Emulsion Co., Ltd.), Noigen XL-400, and Noigen XL-1000F (the above are manufactured by Dai-ichi Kogyo Seiyaku Co., Ltd.).

Specific examples (commercially available products) of POE.POP alkylphenyl ether include Emulgen L40 (manufactured by Kao Corporation), Dispanol KP189-40, and Dispanol KP189R-40 (the above are manufactured by NOF Corporation).

Specific examples (commercially available products) of POE polycyclic phenyl ether include Newcol 714, Newcol 707, Newcol 2609, Newcol 2614 (the above are manufactured by Nippon Nyukazai Co., Ltd.), Emulgen A-60, Emulgen A-90, Emulgen B-66 (the above are manufactured by Kao Corporation), BLAUNON DSP-9, BLAUNON DSP-12.5, BLAUNON TSP-5, and BLAUNON TSP-16 (the above are manufactured by Aoki Oil Industrial Co. Ltd.).

Specific examples (commercially available products) of POE.POP polycyclic phenyl ether include Newcol 2616F, Newcol 710-F, Newcol 2608F, Newcol 707-F (the above are manufactured by Nippon Nyukazai Co., Ltd.), Newkalgen CP-160, and Newkalgen GP-120 (the above are manufactured by Takemoto Oil & Fat Co., Ltd.).

Specific examples (commercially available products) of ethylenediamine POE.POP condensate include ethylenediamine PO40EO40 (manufactured by NOF Corporation) and Pluronic TR-704 (manufactured by Asahi Denka Kogyo Co. Ltd.).

The concentration of the polyoxyethylene nonionic surfactant in a measurement method of the present invention is not particularly limited as long as it is a concentration that enables the measurement method of the present invention, and for example, it is 0.01% to 1%, and preferably 0.05% to 0.2%. In the present invention, the polyoxyethylene nonionic surfactant can be used alone (one kind), or in combination of two or more kinds.

(5) Bile Acid Derivative

The bile acid derivative in the present invention is not particularly limited as long as it enables a measurement of the present invention, and examples include bile acid derivatives having zwitterionic surfactant action and bile acid derivatives having nonionic surfactant action. Examples of bile acid derivatives having zwitterionic surfactant action include 3-[(3-cholamidopropyl)dimethylammonio]propanesulfonic acid (hereinafter abbreviated as CHAPS) and 3-[(3-cholamidopropyl)dimethylammonio]-2-hydroxypropanesulfonic acid (hereinafter abbreviated as CHAPSO).

Examples of bile acid derivatives having nonionic surfactant function include N,N-bis(3-D-gluconamidopropyl) cholamide (hereinafter abbreviated as BIGCHAP) and N,N-bis(3-D-gluconamidopropyl)deoxycholamide (hereinafter abbreviated as deoxy-BIGCHAP).

The bile acid derivative in a measurement method of the present invention is used at a concentration in the range of 1- to 50-times the critical micelle concentration (cmc), and in particular, 1- to 10-times the cmc concentration is preferred. In the present invention, the bile acid derivative can be used alone (one kind), or in combination of two or more kinds.

(6) Antibody and Labeled Antibody

Antibodies in the present invention are not particularly limited as long as they are antibodies that specifically bind to the component to be measured, and while both polyclonal antibodies and monoclonal antibodies can be used, monoclonal antibodies are preferred. Furthermore, the antibodies to be used in the present invention may be antibody fragments with the Fc portions removed, such as Fab obtained by papain treatment of an antibody, $F(ab')_2$ obtained by pepsin treatment of an antibody, and Fab' obtained by pepsin treatment and reduction treatment of an antibody. As antibody fragment, $F(ab')_2$ is preferred.

The antibody in the present invention can be obtained by standard methods using the component to be measured or a peptide corresponding to an epitope thereof as an antigen, and it is also commercially available.

In case the component to be measured is MxA protein, examples of the antibody that specifically binds to MxA protein include anti-human MxA protein monoclonal antibodies KM1122, KM1123, KM1124, KM1125, KM1126, KM1127, KM1128, KM1129, KM1130, KM1131, KM1132, KM1133, KM1134, and KM1135 produced by hybridoma cell lines KM1122, KM1123, KM1124 (FERM BP-4729), KM1125, KM1126, KM1127, KM1128, KM1129, KM1130, KM1131, KM1132 (FERM BP-4730), KM1133, KM1134, and KM1135 (FERM BP-4731), respectively, which are described in International Publication No. WO 96/05230.

The labeled antibody in the present invention is an antibody that may be used in a measurement method of the present invention, and can be produced by a method, described later, using an aforementioned antibody and a labeling substance described below.

(7) Measurement Method

The measurement method of the present invention is a method for measuring a component to be measured, which comprises reacting in the presence of a fatty acid alkanolamide, a component to be measured in a specimen with a first antibody which binds to the component to be measured; then reacting a labeled second antibody, in which a label is bound to a second antibody that binds to the component to be measured, to form an immunocomplex comprising the first antibody, the component to be measured, and the labeled second antibody; and measuring the amount of the label in the formed immunocomplex. Furthermore, the measurement method of the present invention is a method for measuring a component to be measured, which comprises reacting a component to be measured in a specimen with a first antibody which binds to the component to be measured; then reacting in the presence of a polyoxyethylene nonionic surfactant, a labeled second antibody, in which a label is bound to a second antibody that binds to the component to be measured, to form an immunocomplex comprising the first antibody, the component to be measured, and the labeled second antibody; and measuring the amount of the label in the formed immunocomplex. Specific embodiments of the measurement method of the present invention are indicated below.

(1) A method of reacting in the presence of a fatty acid alkanolamide, the component to be measured with a first antibody which binds to the component to be measured (first reaction step); then reacting a labeled second antibody, in which a label is bound to a second antibody that binds to the component to be measured (second reaction step), to form an immunocomplex comprising the first antibody, the component to be measured, and the labeled second antibody; and measuring the amount of the label in the formed immunocomplex (detection step).

(2) A method of reacting the component to be measured with a first antibody which binds to the component to be measured (first reaction step); then reacting in the presence of a polyoxyethylene nonionic surfactant, a labeled second antibody, in which a label is bound to a second antibody that binds to the component to be measured (second reaction step), to form an immunocomplex comprising the first antibody, the component to be measured, and the labeled second antibody; and measuring the amount of the label in the formed immunocomplex (detection step).

(3) A method of reacting in the presence of a fatty acid alkanolamide, the component to be measured with a first antibody which binds to the component to be measured (first reaction step); then reacting in the presence of a polyoxyethylene nonionic surfactant, a labeled second antibody, in which a label is bound to a second antibody that binds to the component to be measured (second reaction step), to form an immunocomplex comprising the first antibody, the component to be measured, and the labeled second antibody; and measuring the amount of the label in the formed immunocomplex (detection step).

In the above-mentioned (1) to (3), the first reaction step can be performed with addition of a bile acid derivative.

In the above-mentioned (1) to (3), an immunocomplex of the component to be measured and the first antibody forms in the first reaction step. In the second reaction step, the labeled second antibody reacts with the immunocomplex of the first antibody and the component to be measured formed in the first reaction step, and an immunocomplex of the first antibody, the component to be measured, and the labeled second antibody is formed. In the detection step, the amount of label in the immunocomplex of the first antibody, the component to be measured, and the labeled second antibody formed in the second reaction step is measured. The concentration of the component to be measured in a specimen used can be determined by performing similar measurements using a standard material, which is the component to be measured with a known concentration, producing a calibration curve showing the relationship between the concentration and the amount of information derived from the label, and correlating the amount of label determined in the detection step with the produced calibration curve.

The standard material can be prepared from a biological sample, and it can also be prepared using recombinant antigens produced by genetic recombination methods. The standard material may take any form such as a solution form or a freeze-dried form, and depending on the form, it may be used after dissolving it at the time of use in an aqueous medium or such described below. Furthermore, when preparing a standard material, a below-described aqueous medium, metal ion, salt, sugar, surfactant, protein, protein stabilizer, and such may be used.

In the above-mentioned measurement methods of (1) and (3), the specimen may be pretreated by mixing the specimen with a fatty acid alkanolamide, or by mixing the specimen with fatty acid alkanolamide and bile acid derivative in advance, and then subjecting the pretreated specimen to reaction with the first antibody. In the above-mentioned measurement method of (2), the specimen may be pretreated by mixing the specimen with a bile acid derivative in advance, and then subjecting the pretreated specimen to reaction with the first antibody.

The measurement method of the present invention can be applied to dry chemistry or to reactions in solutions. The reaction temperature in the first reaction step and the second reaction step is not particularly limited as long as it is a reaction temperature that enables the measurement method of the present invention, and is, for example, 0° C. to 50° C., and preferably 4° C. to 40° C. The reaction time is not particularly limited as long as it is a reaction time that enables the measurement method of the present invention, and is, for example, 1 minute to 72 hours, and preferably 5 minutes to 20 hours.

A washing step may or may not be set up between the first reaction step and the second reaction step, and a washing step is preferably set up. Furthermore, a washing step may or may not be set up between the second reaction step and the detection step, and a washing step is preferably set up. The first antibody may or may not be immobilized (fixed) onto an insoluble carrier, and it is preferably immobilized (fixed). If the first antibody is immobilized (fixed) onto an insoluble carrier, washing of the insoluble carrier after the first reaction step enables separation of the immunocomplex of the first antibody and the component to be measured formed in the first reaction step from unreacted components (components derived from the specimen, excess first antibody, and such). Similarly, washing of the insoluble carrier after the second reaction step enables separation of the immunocomplex of the first antibody, the component to be measured, and the labeled second antibody formed in the second reaction step from unreacted components (excess labeled second antibody, and such). Examples of the washing solution include phosphate buffered saline [10 mmol/L phosphate buffer containing 0.15 mol/L sodium chloride, pH 7.2 (hereinafter indicated as PBS)], PBS containing a surfactant, and aqueous media described below. Examples of the surfactant include nonionic surfactants such as Tween 20.

The insoluble carrier is not particularly limited as long as it can immobilize (fix) the first antibody and enables the antigen-antibody reactions and the detection reaction. Examples of preferred material for the insoluble carrier include polymer materials such as polystyrene, polycarbonate, polyvinyl toluene, polypropylene, polyethylene, polyvinyl chloride, nylon, polymethacrylate, gelatin, agarose, cellulose, nitrocellulose, cellulose acetate, acetylcellulose, and polyethylene terephthalate; glass; ceramics; magnetic particles; and metals. Examples of the preferred shape of the insoluble carrier include tube, bead, plate, microparticle such as latex, stick, and such, and a polystyrene microtiter plate having 96 wells per plate or such is preferred.

Methods of immobilizing (fixing) the first antibody to an insoluble carrier include known methods, such as methods using a physical bond, methods using a chemical bond, or a combination thereof. Examples of the physical bond include electrostatic bonds, hydrogen bond, and hydrophobic bonds. Examples of the chemical bond include covalent bonds and coordinate bonds. When using a polystyrene microtiter plate as the insoluble carrier, an example includes a method of fixing in which addition of a solution of a first antibody to the wells of the plate is followed by incubation for one hour to one day at 4° C. to 30° C. for physical adsorption.

The first antibody can be immobilized (fixed) directly or indirectly onto the insoluble carrier. Examples of the indirect immobilization (fixation) include a method in which a solution of a biotinylated first antibody is added to an insoluble carrier fixed with avidin, and the first antibody is fixed onto the insoluble carrier through specific binding between biotin and avidin. Furthermore, an antibody that specifically binds to the first antibody may be fixed onto the insoluble carrier and the first antibody may be fixed onto the insoluble carrier via this antibody. Alternatively, the first antibody may be fixed onto the insoluble carrier by covalent bonds via a linker. The linker is, for example, a molecule that can covalently bind with both a functional group on the first antibody and a functional group on the surface of the insoluble carrier. Molecules bearing, within the same molecule, a first reactive group that can react with a functional group of the first antibody and a second reactive group that can react with a functional group on the surface of the insoluble carrier are preferred, and among them, molecules in which the first reactive group and the second reactive group are different groups are particularly preferred. Examples of the functional group of the first antibody and the functional group on the surface of the insoluble carrier include a carboxyl group, an amino group, a glycidyl group, a sulfhydryl group, a hydroxy group, an amido group, an imino group, an N-hydroxysuccinyl group, and a maleimide group. Examples of the reactive group on the linker include groups such as arylazide, carbodiimide, hydrazide, aldehyde, hydroxymethyl phosphine, imide ester, isocyanate, maleimide, N-hydroxy succinimide (NHS) ester, pentafluorophenyl (PFP) ester, psoralen, pyridyl disulfide, and vinyl sulfone.

When the first antibody is not immobilized (fixed) onto an insoluble carrier, the reaction solution after the first reaction step can be run through an insoluble carrier onto which a substance that can react with the first antibody is immobilized (fixed), and then the immunocomplex comprising the first antibody and the component to be measured can be separated from the unreacted components (components derived from the specimen, excess first antibody, and such) by washing the insoluble carrier. The substance which can react with the first antibody can be immobilized (fixed) onto the insoluble carrier by a method similar to the aforementioned method for immobilizing (fixing) the first antibody to the insoluble carrier.

Examples of the labeling substance for labeling the second antibody include enzymes, fluorescent substances, luminescent substances, radioisotopes, biotin, digoxigenin, polypeptides containing a tag sequence, metallic colloid particles, and colored latex particles. Examples of enzymes include alkaline phosphatase, peroxidase, galactosidase, glucuronidase, and luciferase. Examples of fluorescent substances include fluorescein isothiocyanate (FITC) and rhodamine B-isothiocyanate (RITC). Examples of other fluorescent substances include quantum dot (Science, 281, 2016-2018, 1998), phycobiliproteins such as phycoerythrin, and fluorescence-emitting proteins such as green fluorescent protein (GFP), red fluorescent protein (RFP), yellow fluorescent protein (YFP), and blue fluorescent protein (BFP). Examples of luminescent substances include acridinium and derivatives thereof, a ruthenium complex compound, and lophine. As to the ruthenium complex compound, a compound that electrochemically emits light with electron donors, described in Clin. Chem. 37, 9, 1534-1539, 1991, is preferred. Examples of radioisotopes include $^{3}H$, $^{14}C$, $^{35}S$, $^{32}P$, $^{125}I$, and $^{131}I$.

Examples of polypeptides containing a tag sequence include the FLAG peptide (FLAG tag, Asp Tyr Lys Asp Asp Asp Asp Lys), polyhistidine (His tag, His His His His His His), myc epitope peptide (myc tag, Glu Gln Lys Leu Ile Ser Glu Glu Asp Leu), and hemagglutinin epitope peptide (HA tag, Tyr Pro Tyr Asp Val Pro Asp Tyr Ala).

Labeling of the second antibody can be carried out by a reaction to form a covalent bond between the functional group of the second antibody and the functional group of the labeling substance, either with or without a linker. Examples of the functional group include a carboxyl group, an amino group, a glycidyl group, a sulfhydryl group, a hydroxy group, an amido group, an imino group, a hydroxysuccinyl ester group, a maleimide group, and an isothiocyanate group. A condensation reaction between these functional groups can be performed.

Examples of a linking method without a linker include a method using a carbodiimide compound such as EDC. In this case, an active ester such as NHS or its derivatives can be used. The condensation reaction between an isothiocyanate group and an amino group is preferred because it does not require other reagents, and proceeds simply by mixing under neutral to weakly alkaline conditions.

Examples of the linker include molecules having both of a functional group to react with a functional group of the second antibody and a functional group to react with a functional group of the labeling substance. The linker is preferably a molecule that has, within the same molecule, a first functional group to react with an amino acid residue of the second antibody, and a second functional group to react with a functional group of the labeling substance. Among these, molecules in which the first functional group is a different group from the second functional group are particularly preferred. Examples of the functional group of the linker include the functional groups described above.

Examples of methods for chemically linking a radioisotope include methods described in the literature (Antibody Immunoconj. Radiopharm., 3, 60, 1990).

In case the labeling substance is polypeptide such as an enzyme, avidin, a fluorescence-emitting protein, a phycobiliprotein, and a polypeptide containing a tag sequence, production can be carried out by producing an expression vector containing a DNA that encodes a fusion protein of the labeling substance and the antibody, introducing the expression vector into a suitable host, and culturing the host according to the known genetic recombination techniques (Molecular Cloning: A Laboratory Manual, 3rd Edition, Cold Spring Harbor Laboratory Press, 2001). A DNA encoding the fusion protein can be obtained by cloning each of the DNA encoding the antibody and the DNA encoding the labeling substance by using PCR or the like, and linking each of the DNAs by a ligase reaction.

The amount of label in the immune complexes of the first antibody, the component to be measured, and the labeled second antibody formed in the second reaction step is measured in the detection step. Suitable methods can be selected according to the labeling substance for measurement of the label amount. In the case the labeling substance is a coloring substance, i.e. a substance that absorbs light of a certain wavelength, a spectrophotometer, a multi-well plate reader, or such can be used. In the case the labeling substance is a fluorescent substance, a spectrofluorometer, fluorescence multi-well plate reader, or such may be used. When the labeling substance is a luminescent substance, a luminescence photometer, luminescence multi-well plate reader, or such can be used. In the case the labeling substance is a radioisotope, the amount of radioisotope can be determined by measuring the radioactivity using a scintillation counter, a γ-well counter, or such.

In the case the label is an enzyme, measuring the amount of the label means measuring the enzyme activity. The amount of the label can be measured by reacting a substrate of the enzyme with the enzyme and measuring the formed product. In the case the enzyme is peroxidase, peroxidase activity can be measured, for example, by absorbance methods, fluorescence methods, luminescence methods, or such. Examples of a method of measuring peroxidase activity by an absorbance method include a method in which peroxidase is reacted with a combination of hydrogen peroxide and an oxidative coloring chromogen, which are substrates of peroxidase, and the absorbance of the reaction solution is measured using a spectrophotometer, multi-well plate reader, or the like. Examples of the oxidative coloring chromogen include a leuco-type chromogen and an oxidative coupling-coloring chromogen.

The leuco-type chromogen is a substance that is converted into a dye by itself in the presence of hydrogen peroxide and a peroxidative substance such as peroxidase. Specific examples include tetramethylbenzidine, o-phenylenediamine, 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino) diphenylamine sodium salt (DA-64), 4,4'-bis(dimethylamino)diphenylamine, and bis[3-bis(4-chlorophenyl)methyl-4-dimethylaminophenyl]amine (BCMA).

The oxidative coupling-coloring chromogen is a substance that forms a dye by oxidative coupling of two compounds in the presence of hydrogen peroxide and a peroxidative substance such as peroxidase. Examples of the combination of two compounds include a combination of a coupler and an aniline compound (Trinder reagent), and a combination of a coupler and a phenol compound. Examples of the coupler include 4-aminoantipyrine (4-AA) and 3-methyl-2-benzothiazolinonehydrazine. Examples of the aniline compound include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine, and N-ethyl-N-(2-hydroxy-3-sulfopropyl)-4-fluoro-3,5-dimethoxyaniline (F-DAOS). Examples of the phenol compound include phenol, 4-chlorophenol, 3-methylphenol, and 3-hydroxy-2,4,6-triiodobenzoic acid (HTIB).

Examples of the method of measuring peroxidase activity by a fluorescence method include a method in which peroxidase is reacted with a combination of hydrogen peroxide and a fluorescent substance, which are substrates of peroxidase, and the intensity of the generated fluorescence is measured using a spectrofluorometer, fluorescence multi-well plate reader, or the like. Examples of the fluorescent substance include 4-hydroxyphenylacetic acid, 3-(4-hydroxyphenyl) propionic acid, and coumarin.

Examples of the method of measuring peroxidase activity by a luminescence method include a method in which peroxidase is reacted with a combination of hydrogen peroxide and a luminescent substance, which are substrates of peroxidase, and the intensity of the generated luminescence is measured using a luminescence intensity meter, luminescence multi-well plate reader, or the like. Examples of the luminescent substance include a luminol compound and a lucigenin compound.

In the case the enzyme is alkaline phosphatase, the alkaline phosphatase activity can be measured by, for example, a luminescence method. Examples of a method of measuring alkaline phosphatase activity by a luminescence method include a method in which alkaline phosphatase is reacted with its substrate, and the luminescence intensity of the generated luminescence is measured using a luminescence intensity meter, luminescence multi-well plate reader, or the like. Examples of the substrate of alkaline phosphatase include 3-(2'-spiroadamantane)-4-methoxy-4-(3'-phosphoryloxy)phenyl-1,2-dioxetane disodium salt (AMPPD), 2-chloro-5-{4-methoxyspiro[1,2-dioxetane-3,2'-(5'-chloro)tricyclo[3.3.1.13,7]decane]-4-yl}phenylphosphate disodium salt (CDP-Star™), 3-{4-methoxyspiro[1,2-dioxetane-3,2'-(5'-chloro)tricyclo[3.3.1.13,7]decane]-4-yl}phenylphosphate disodium salt (CSPD™), and [10-methyl-9(10H)-acridinylidene]phenoxymethylphosphate disodium salt (Lumigen™ APS-5).

In the case the enzyme is β-D-galactosidase, the β-D-galactosidase activity can be measured by, for example, an absorbance method (colorimetric method), a luminescence method, or a fluorescence method. Examples of the method of measuring β-D-galactosidase activity by an absorbance method (colorimetric method) include a method using o-nitrophenyl-β-D-galactopyranoside. Examples of the method of measuring β-D-galactosidase activity by a luminescence method include a method in which β-D-galactosidase is reacted with its substrate and the luminescence of the reaction solution is measured by a luminescence intensity meter, luminescence multi-well plate reader, or the like. Examples of the substrate of β-D-galactosidase include Galacton-Plus (manufactured by Applied Biosystems), and analogs thereof. Examples of the method for measuring β-D-galactosidase activity by a fluorescence method include a method in which β-D-galactosidase is reacted with its substrate and the fluorescence of the reaction solution is measured with a spectrofluorometer, fluorescence multi-well plate reader, or the like. Examples of the substrate of β-D-galactosidase include 4-methylumbeliferyl-β-D-galactopyranoside.

In the case the enzyme is luciferase, the luciferase activity can be measured, for example, by a luminescence method. Examples of the method for measuring luciferase activity by a luminescence method include a method in which luciferase is reacted with its substrate and the luminescence of the reaction solution is measured with a luminescence intensity meter, luminescence multi-well plate reader, or the like. Examples of the substrate of luciferase include luciferin and coelenterazine.

When the labeling substance is a substance (referred to as substance A) other than a fluorescent substance, a luminescent substance, a radioisotope, or an enzyme, a labeled substance B, which is a substance (substance B) specifically binding to substance A and labeled with a fluorescent substance, a luminescent substance, a radioisotope, an enzyme, or such, is reacted with the immunocomplex of the first antibody, the component to be measured, and the labeled second antibody (i.e., the second antibody labeled with substance A) formed in the second reaction step to form an immunocomplex of the first antibody, the component to be measured, the labeled second antibody (i.e., the second antibody labeled with substance A), and the labeled substance B; then the component to be measured in the specimen can be measured by measuring the amount of label in this formed immunocomplex by an aforementioned method. Examples of the substance B include antibodies against substance A, avidin, (when substance A is biotin), streptavidin (when substance A is biotin), and biotin (when substance A is avidin or streptavidin). The antibody against substance A may be an antibody fragment, and examples of an antibody fragment include the aforementioned Fab, F(ab')$_2$, and Fab'.

Meanwhile, the first reaction step of the measurement methods (1) and (2) of the present invention can also be applied to competition methods. Specifically, the following embodiments can be presented as examples of competition method:

(4) A method of reacting, in the presence of a fatty acid alkanolamide, the component to be measured with a labeled competitive substance, in which a label is bound to a competitive substance, and an antibody that binds to both the component to be measured and the labeled competitive substance (competitive reaction step); and measuring the amount of the label in the formed immunocomplex of the labeled competitive substance and the antibody (detection step).

(5) A method of reacting, in the presence of a fatty acid alkanolamide, the component to be measured with a competitive substance and a labeled antibody, in which a label is bound to an antibody that binds to both the component to be measured and the competitive substance (competitive reaction step); and measuring the amount of the label in the formed immunocomplex of the competitive substance and the labeled antibody (detection step).

The competitive reaction step can be performed with addition of a bile acid derivative. A washing step may or may not be set up between the competitive reaction step and the detection step, and a washing step is preferably set up. Examples of the washing step include the washing steps in the aforementioned assaying methods (1) to (3).

In the above-mentioned method of (4), the antibody that binds to both the component to be measured and the labeled competitive substance may or may not be immobilized (fixed) onto an insoluble carrier, and it is preferably immobilized (fixed). Furthermore, in the above-mentioned method of (5), the competitive substance may or may not be immobilized (fixed) onto an insoluble carrier, and it is preferably immobilized (fixed).

The competitive reaction step may be carried out in the presence or absence of an aqueous medium, and is preferably carried out in the presence of an aqueous medium. Examples of the aqueous medium include the below-described aqueous media and such. Herein, a competitive substance means a substance which can bind to an "antibody that binds to the component to be measured" and whose binding is competitive with the component to be measured, and includes the component to be measured itself. A competitive substance is used when measuring a component to be measured in a specimen by a competition method. Therefore, the antibody, which binds to a component to be measured, used in the competition method is an antibody which binds to the component to be measured and the competitive substance, and while it forms an immunocomplex by binding to the component to be measured, it also forms an immunocomplex by binding to the competitive substance.

The competitive substance is preferably a substance having a structure that is identical to an epitope recognized by the antibody that binds to the component. In addition, it is preferably a competitive substance whose binding strength toward the antibody that binds to the component to be measured is comparable to the binding strength of the component toward the antibody. The component to be measured itself is preferred as competitive substance. A labeled competitive substance can be prepared using the competitive substance and an aforementioned labeling substance by a method similar to that for the aforementioned labeled second antibody.

Examples of the aqueous medium used in the present invention include deionized water, distilled water, and buffer, and a buffer is preferred. A buffer agent used for preparing a buffer is not particularly limited as long as it has buffering ability. Examples of the buffer include a buffer with pH 1 to 11, such as lactate buffer, citrate buffer, acetate buffer, succinate buffer, phthalate buffer, phosphate buffer, triethanolamine buffer, diethanolamine buffer, lysine buffer, barbiturate buffer, imidazole buffer, malate buffer, oxalate buffer, glycine buffer, borate buffer, carbonate buffer, glycine buffer, or Good's buffer.

Examples of the Good's buffer include 2-morpholinoethanesulfonic acid (MES) buffer, bis(2-hydroxyethyl)iminotris(hydroxymethyl)methane (Bis-Tris) buffer, tris(hydroxymethyl)aminomethane (Tris) buffer, N-(2-acetoamido) imino diacetic acid (ADA) buffer, piperazine-N,N'-bis(2-ethanesulfonic acid) (PIPES) buffer, 2-[N-(2-acetamido) amino]ethanesulfonic acid (ACES) buffer, 3-morpholino-2-hydroxypropanesulfonic acid (MOPSO) buffer, 2-[N,N-bis (2-hydroxyethyl)amino]ethanesulfonic acid (BES) buffer, 3-morpholinopropanesulfonic acid (MOPS) buffer, 2-{N-[tris(hydroxymethyl)methyl]amino}ethanesulfonic acid (TES) buffer, N-(2-hydroxyethyl)-N'-(2-sulfoethyl)piperazine (HEPES) buffer, 3-[N,N-bis(2-hydroxyethyl)amino]-2-hydroxypropanesulfonic acid (DIPSO) buffer, 2-hydroxy-3-{[N-tris(hydroxymethyl)methyl]amino}propanesulfonic acid (TAPSO) buffer, piperazine-N,N'-bis(2-hydroxypropane-3-sulfonic acid) (POPSO) buffer, N-(2-hydroxyethyl)-N'-(2-hydroxy-3-sulfopropyl)piperazine (HEPPSO) buffer, N-(2-hydroxyethyl)-N'-(3-sulfopropyl)piperazine (EPPS) buffer, tricine[N-tris(hydroxymethyl)methylglycine] buffer, vicine[N,N-bis(2-hydroxyethyl)glycine] buffer, 3-[N-tris (hydroxymethyl)methyl]aminopropanesulfonic acid (TAPS) buffer, 2-(N-cyclohexylamino)ethanesulfonic acid (CHES) buffer, 3-(N-cyclohexylamino)-2-hydroxypropanesulfonic acid (CAPSO) buffer, and 3-(N-cyclohexylamino)propanesulfonic acid (CAPS) buffer.

The concentration of the buffer is not particularly limited as long as it is a concentration suitable for the measurement, and is preferably 0.001 to 2.0 mol/L, more preferably 0.005 to 1.0 mol/L, and particularly preferably 0.01 to 0.1 mol/L.

In the measurement method of the present invention, a metal ion, a salt, a sugar, an antiseptic agent, a protein, a protein stabilizer, or such can concomitantly be present. Examples of the metal ion include magnesium ion, manganese ion, and zinc ion. Examples of the salt include sodium chloride and potassium chloride. Examples of the sugar include mannitol and sorbitol. Examples of the antiseptic agent include sodium azide, an antibiotic (streptomycin, penicillin, gentamicin, etc.), BioAce, Proclin 300, and Proxel GXL. Examples of the protein include bovine serum albumin (BSA), fetal bovine serum (FBS), casein, and BlockAce (manufactured by Dainippon Pharmaceutical Co., Ltd.). Examples of the protein stabilizer include Peroxidase Stabilizing Buffer (manufactured by DakoCytomation).

(8) Kit for Measurement

A kit for measurement of the present invention is a kit for immunologically measuring a component to be measured in a specimen and can be used for the measurement methods of the present invention.

The kit for measurement of the present invention is a kit for measurement which comprises a first reagent comprising a first antibody which binds to a component to be measured and a fatty acid alkanolamide; and a second reagent comprising a labeled second antibody, in which a label is bound to a second antibody that binds to the component to be measured. Furthermore, the kit for measurement of the present invention is a kit for measurement which comprises a first reagent comprising a first antibody which binds to a component to be measured; and a second reagent comprising a labeled second antibody, in which a label is bound to a second antibody that binds to the component to be measured, and a polyoxyethylene nonionic surfactant. Specific embodiments of the kit for measuring of the present invention are indicated below.

(1) A kit for measuring a component to be measured in a specimen, which comprises a first reagent comprising a first antibody which binds to a component to be measured and a fatty acid alkanolamide; and a second reagent comprising a labeled second antibody, in which a label is bound to a second antibody that binds to the component to be measured.

(2) A kit for measuring a component to be measured in a specimen, which comprises a first reagent comprising a first antibody that binds to a component to be measured; and a second reagent comprising a labeled second antibody, in which a label is bound to a second antibody that binds to the component to be measured, and a polyoxyethylene nonionic surfactant.

(3) A kit for measuring a component to be measured in a specimen, which comprises a first reagent comprising a first antibody which binds to a component to be measured and a fatty acid alkanolamide; and a second reagent comprising a labeled second antibody, in which a label is bound to a second antibody that binds to the component to be measured, and a polyoxyethylene nonionic surfactant.

The first reagent may contain a bile acid derivative.

In the abovementioned kits of (1) and (3), the first reagent may take a form in which a reagent comprising the fatty acid alkanolamide [first reagent (A)], and a reagent comprising the first antibody that binds to a component to be measured [first reagent (B)] are stored separately. In the abovementioned kits of (1) and (3), when a bile acid derivative is included in the first reagent, the first reagent may take a form in which a reagent comprising the fatty acid alkanolamide and the bile acid derivative [first reagent (A)], and a reagent comprising a first antibody that binds to a component to be measured [first reagent (B)] are stored separately. In the above-mentioned kit of (2), when a bile acid derivative is included in the first reagent, the first reagent may take a form in which a reagent comprising the bile acid derivative [first reagent (A)], and a reagent comprising the first antibody that binds to a component to be measured [first reagent (B)] are stored separately. Herein, the first reagent (A) can be used as a specimen pretreatment solution.

The form of the kit of the present invention may be any form, such as a solution form or a freeze-dried form. Examples of each of the first antibody, the labeled second antibody, the fatty acid alkanolamide, the polyoxyethylene nonionic surfactant, and the bile acid derivative of the kit of the present invention include those mentioned above. Furthermore, a kit of the present invention may include the aforementioned aqueous medium, metal ion, salt, sugar, antiseptic agent, protein, protein stabilizer, or such as necessary.

Hereinbelow, the present invention will be specifically described with reference to the Examples, which is not to be construed as limiting the scope of the present invention.

Example 1

[1] Preparation of Anti-MxA Protein Monoclonal Antibodies

Two types of anti-human MxA protein monoclonal antibodies, KM1124 (WO 96/05230) and KM1135 (WO 96/05230), with distinct epitopes were prepared as described below. KM1124 is a mouse monoclonal antibody which binds to the epitope present in residues 220 to 297 counting from the amino terminus of human MxA protein, and KM1135 is a mouse monoclonal antibody which binds to the epitope present in residues 10 to 220 counting from the amino terminus of human MxA protein.

A hybridoma cell line KM1124 (FERM BP-4729) which produces the monoclonal antibody KM1124 and a hybridoma cell line KM1135 (FERM BP-4731) which produces the monoclonal antibody KM1135 were individually intraperitoneally injected into pristane-treated 8-week old nude female mice (Balb/c) at 5 to 20×10$^6$ cells/animal. The hybridoma cell lines cancerated in the ascites after 10 to 21 days, and the ascitic fluids were collected from mice in which the ascitic fluids had accumulated. The collected ascitic fluids were centrifuged at 3000 rpm for five minutes to remove the solid content, and the supernatants were collected. The monoclonal antibodies purified by the caprylic acid precipitation method (Antibodies-A Laboratory Manual, Cold Spring Harbor Laboratory, 1988) from these supernatants were used in the method for immunologically measuring MxA protein.

[2] Preparation of Recombinant MxA Protein

With a human MxA protein expression vector pET 14b-MxA (Nucleic Acids Res., 32, 643-652, 2004) produced by inserting an NdeI-BamHI fragment containing a cDNA encoding human MxA protein (prepared based on a nucleotide sequence registered in Genbank as BC032602) between NdeI and BamHI of the pET-14b vector (manufactured by Novagen, EMD Biosciences), was transformed the *Escherichia coli* BL21 (DE3) pLysS strain. This transformant expresses an MxA protein to which an N-terminal His tag has been added.

The obtained transformant was inoculated into 5 mL of LB medium containing ampicillin, and culture was carried out with shaking at 37° C. until the optical density at 600 nm (OD600) reached 0.5. This culture solution was inoculated into 250 mL of LB medium containing ampicillin, and culture was carried out with shaking at 37° C. until the optical density at 600 nm reached 0.3 to 0.5. To this culture, isopropylthiogalactoside (IPTG) was added at a final concentration of 0.4 mmol/L, and culture was further carried out for two hours with shaking at 37° C. The obtained culture solution was centrifuged at 4° C. at 3000 rpm for ten minutes to collect the bacterial cells. The bacterial cells were stored at −80° C. until MxA protein preparation.

Since MxA protein was present in the bacterial cells in the form of inclusion bodies, the bacterial cells were thawed on ice, and 20 mL of ice-cooled binding buffer (5 mmol/L imidazole, 0.5 mol/L sodium chloride, 20 mmol/L Tris-HCl, pH 7.9) was added to give a suspension. The bacterial cell suspension was subjected to five times of 30-second ultrasonic treatment to disrupt the cells, and then centrifuged at 4° C. at 4000 rpm for ten minutes. The supernatant was removed, and the precipitate was suspended in 20 mL of added ice-cooled binding buffer. Similarly, ultrasonic treatment and centrifugation were again performed. The supernatant was removed, and 20 mL of the binding buffer containing 6 mon urea was added to the precipitate to give a suspension. After a similar ultrasonic treatment, the mixture was left to stand on ice for 30 minutes to dissolve the inclusion bodies, and then centrifuged at 4° C. at 10,000 rpm for 30 minutes. The supernatant was collected and then filtered through a 0.45-nm millipore filter.

To the obtained solution, 0.5 mL of Ni-NTA His.Bind Resin (manufactured by Novagen, EMD Biosciences) was added, then the whole was mixed while rotating at 4° C. for two hours, and the MxA protein was allowed to bind with the resin via the His tag. This mixture was centrifuged at 4° C. at 3000 rpm for two minutes to recover the resin. After adding 10 mL of ice-cooled binding buffer containing 6 mol/L urea to the resin, the whole was centrifuged at 4° C. at 3000 rpm for two minutes to recover the resin. After repeating this washing operation, 10 mL of ice-cooled washing buffer (6 mol/L urea, 60 mmol/L imidazole, 0.5 mol/L sodium chloride, 20 mmol/L Tris-HCl, pH 7.9) was further added to the resin, and the whole was centrifuged at 4° C. at 3000 rpm for two minutes to recover the resin.

10 mL of ice-cooled elution buffer (6 mol/L urea, 1 mol/L imidazole, 0.5 mol/L sodium chloride, 20 mmol/L Tris-HCl, pH 7.9) was added to the resin, and the whole was mixed while rotating at 4° C. for two hours to elute the MxA protein from the resin. This mixture containing the resin was centrifuged at 4° C. at 3000 rpm for two minutes, and the supernatant MxA protein solution was collected. The collected MxA protein solution was used to prepare a standard solution for measuring the MxA protein.

[3] Preparation of Native MxA Protein

Adhesive human glioblastoma-derived cell line T98G (purchased from DS Pharma Biomedical Co., Ltd., J. Cell. Physiol., 99, 43-54, 1979) was cultured for two to three days in a 10-mL flask for cell culture added with 10 mL of E-MEM medium (manufactured by Wako Pure Chemical Industries, Ltd.) supplemented with 10% fetal bovine serum (FBS), 1% nonessential amino acids (manufactured by Invitrogen), and 1 mmol/L sodium pyruvate (manufactured by Invitrogen), using a carbon dioxide gas incubator (5% CO2, 37° C.) until confluency was reached. When the cells became confluent, the cells were transferred to a 150-cm$^2$ flask and cultured similarly. When the cells became confluent in the 150-cm$^2$ flask, the medium was removed by aspiration, the cells were washed using PBS (−) (phosphate buffer containing neither calcium nor magnesium), and then washed by addition of 0.02% EDTA. Next, after removing the cells by adding a 0.25% trypsin solution, the action of trypsin was stopped by adding an equal amount of the culture medium. The cells were collected and centrifuged (1,400 rpm) at 25° C. for three minutes. The number of cells was counted, the cells were suspended at about 1×10$^5$ cells/ml, in a 150-cm$^2$ flask containing fresh culture medium, and Interferon alpha A protein (Funakoshi) was added to give a 2,000 U/mL solution of Interferon alpha A protein. The cells were cultured for 24 hours using a carbon dioxide gas incubator, the medium was removed by aspiration, the cells were washed using PBS (−), and then washed by addition of 0.02% EDTA. Next, after removing the cells by adding a 0.25% trypsin solution, the action of trypsin was stopped by adding an equal amount of the culture medium. The cells were collected and centrifuged (1,400 rpm) at 25° C. for three minutes. The supernatant was removed, 0.5 mL of hypotonic buffer (10 mmol/L HEPES, 1.5 mmol/L MgCl$_2$, 10 mmol/L KCl) was added and the cells suspended, the solution was collected, and this was stored at −80° C. until use.

[4] Preparation of Anti-MxA Protein Antibody-Immobilized Plate

The anti-MxA protein monoclonal antibody KM1135 prepared in [1] was diluted with a 100 mmol/L phosphate buffer containing 100 mmol/L sodium chloride (pH 7.5) to a concentration of 5 μg/mL, and the mixture was dispensed in a 96-well microtiter plate (manufactured by Nalge Nunc International) at 100 μL/well. After allowing the plate to stand for three days, the supernatant was removed by suction, 300 μL of a pH7.2 phosphate buffer containing 1% BlockAce (manufactured by Dainippon Pharmaceutical Co., Ltd.) and 50 mmol/L sodium chloride were dispensed into each well, and blocking was carried out at room temperature by allowing the plate to stand overnight. After removing the blocking solution, washing was carried out using PBS. The plate after drying for three days using a vacuum dryer was used as anti-MxA protein monoclonal antibody-immobilized plate.

[5] Preparation of Peroxidase-Labeled Anti-MxA Protein Antibody

The anti-MxA protein monoclonal antibody KM1124 prepared in [1] was allowed to bind with peroxidase (hereinafter, abbreviated as POD) by the maleimide method as described below to give a POD-labeled anti-MxA protein antibody.

First, a phosphate buffer containing 2 mg of KM1124 prepared in [1] was replaced with 0.1 mol/L of borate buffer (pH 8.0), and this was concentrated to a volume of 1 mL using an Amicon stirred cell (manufactured by Millipore). 40 μL of 0.1 mol/L borate buffer (pH 8.0) containing 2.15 mg/mL of 2-iminothiolane hydrochloride salt (manufactured by Pierce) was added to the concentrated solution, and after stirring, incubation was carried out for 30 minutes at 30° C. In the above-mentioned reaction, 2-iminothiolane hydrochloride salt was used at a molar ratio of 50 times with respect to KM1124. The reacted solution was subjected to gel filtration using a Sephadex G25 (manufactured by Amersham Bioscience) column (1.5-cm diameter×30 cm) equilibrated with a 0.1 mol/L phosphate buffer (pH6.0) supplemented with 5 mmol/L disodium ethylenediamine tetraacetate (EDTA.2Na), to remove the unreacted 2-iminothiolane hydrochloride salt, and to collect the sulfhydrylated KM1124. The collected solution was concentrated to a volume of 5 mL using an Amicon stirred cell.

On the other hand, 2.5 mg of POD (manufactured by Toyobo Co., peroxidase I-C) corresponding to a molar ratio of 5 times with respect to KM1124 was dissolved in 250 μL of 0.1 mol/L phosphate buffer (pH 7.0). After warming this solution at 30° C. for 5 minutes, 36 μL of a solution of 20 mg/mL of N-(6-maleimidecaproyloxy)succinimide (EMCS, manufactured by Dojindo Laboratories) in N,N-dimethylformamide (manufactured by Nacalai Tesque) was added and stirred, and incubation was carried out at 30° C. for 30 minutes. In the above-mentioned reaction, EMCS was used at a molar ratio of 40 times with respect to POD. The reacted solution was subjected to gel filtration using a Sephadex G25 column (1.5-cm diameter×30 cm) equilibrated with 0.1 mol/L phosphate buffer (pH6.0) to remove the unreacted EMCS, and to collect the maleimidized POD. The collected solution was concentrated using an Amicon stirred cell.

A solution of the sulthydrylated KM1124 obtained as described above and a solution of the maleimidized POD were mixed, this was concentrated to a volume of 2 mL using an Amicon stirred cell, then incubation was carried out at 30° C. for one hour. The obtained labeled antibody was stored at −80° C. until use.

[6] Preparation of a Specimen Diluent and Standard Solutions

A specimen diluent having the following composition was prepared.

| | |
|---|---|
| HEPES (manufactured by Dojindo Laboratories) (pH 8.0) | 0.1 mol/L |
| CHAPS (manufactured by Dojindo Laboratories) | 4.9% |
| Surfactant | (type and concentration described in Table 1) |
| Sodium Chloride | 1.5 mol/L |
| BSA (manufactured by InterGen) | 0.1% |
| Sodium Azide | 0.1% |

The recombinant MxA protein solution prepared in the aforementioned [2] was diluted using the above-described specimen diluent to prepare solutions of MxA protein at each of the concentrations of 0 (specimen diluent only), 0.375, 0.75, 1.5, 3, 6, 12, and 24 ng/mL, and these solutions were used as standard solutions.

[7] Production of a Calibration Curve

100 μL of a standard solution produced in [6] was added to an anti-MxA protein antibody (KM1135)-fixed plate produced in the aforementioned [4] and incubated for one hour to let the MxA protein bind to the antibody. After removing the reaction solution, the washing operation of adding 400 μL of a washing solution [PBS containing 0.05% Tween 20 (manufactured by Kanto Chemical)] and then removing it was performed five times. Next, the POD-labeled anti-MxA protein antibody (KM1124) produced in [5] was diluted 800-fold with a POD-labeled antibody diluent (liquid composition) buffer [50 mmol/L Bis-Tris (manufactured by Dojindo Laboratories), 0.1% BSA (manufactured by InterGen), 0.01% 4-aminoantipyrine (4-AA; manufactured by Salkyo Kasei), 0.035% Proclin 300 (manufactured by Sigma), and 0.1% Nonidet P40], 100 μL of this was added and incubation was carried out for 30 minutes. The reaction solution was removed, and a washing operation of adding 400 μL of the aforementioned washing solution to wash the plate and then removing the washing solution was performed five times. 100 μL of a chromogenic substrate for POD, TMBlue (manufactured by Serological), which contains 0.05% tetramethylbenzidine and hydrogen peroxide was added in the dark and incubation was carried out at room temperature for ten minutes. The reaction was stopped by adding 100 μL of 0.5 mol/L sulfuric acid and incubating at room temperature for ten minutes. The absorbance at a wavelength of 450 nm was measured using a plate reader. By a series of such operations, a calibration curve showing the relationship between the MxA protein concentration and the absorbance was produced.

Next, similar operations were performed using, instead of the aforementioned standard solutions, cultured cells or whole blood samples as specimen. The measured value for each specimen was obtained and the obtained measured values were correlated with the calibration curve produced in advance to determine the MxA protein concentration in each specimen.

[8] Examination of the Variation in Measured Values in MxA Protein Measurements—1 (Primary Reaction)

The adhesive human glioblastoma-derived cell line T98G used in the aforementioned [3] was stimulated with interferon to induce the MxA protein and the native MxA protein was obtained. By comparing the reactivities of the obtained native MxA protein and those of the recombinant MxA protein, the difference in the reactivity of an antibody against a recombinant MxA protein and the reactivity of an antibody against the native MxA protein was examined.

The native MxA protein produced in the aforementioned [3] was diluted 20-fold using the specimen diluent of [6], this was left to stand for 30 minutes to solubilize the cells, then this was further diluted eight-fold with the specimen diluent to give the sample for measurement.

This sample and the standard solutions at each concentration prepared in [6] of the Example were used as specimen, and measurements were carried out by following the operations described in [7]. Specifically, the primary reaction was performed at both 25° C. and 37° C., and the secondary reaction and the chromogenic reaction were performed at 25° C. Herein, the measurement variabilities of the native MxA protein when reacted at 25° C. and when reacted at 37° C. were calculated by the following equation (I). The results are shown Table 1.

[Equation 1]

$$\text{Variability (\%)} = [(\text{native MxA protein concentration when reacted at } 37° \text{ C.})/(\text{native MxA protein concentration when reacted at } 25° \text{ C.}) - 1] * 100 \quad (I)$$

Comparative Example 1

The measurement variability due to the reaction temperature was calculated by a similar method as in Example 1, using a specimen diluent having the same composition as the specimen diluent of [6] in Example 1, except that 1.2% Nonidet P40 (polyoxyethylene alkylphenyl ether) was used as the surfactant in the composition. The results are shown in Table 1.

TABLE 1

| SURFACTANT | CONCENTRATION (%) | MxA PROTEIN CONCENTRATION* | | MEASUREMENT VARIABILITY (%) |
| --- | --- | --- | --- | --- |
| | | REACTION AT 25° C. | REACTION AT 37° C. | |
| AMINON PK-03S | 1.2 | 315.0 | 357.6 | 13.5 |
| STAFOAM F | 1.2 | 320.2 | 372.4 | 16.3 |
| STAFOAM DO | 1.2 | 399.4 | 422.7 | 5.8 |
| STAFOAM DOS | 1.2 | 475.8 | 487.5 | 2.5 |
| STAFOAM T | 1.2 | 368.8 | 426.3 | 15.6 |
| STAFOAM DFC | 1.2 | 315.4 | 386.4 | 22.5 |
| STAFOAM DF4 | 1.2 | 348.9 | 379.3 | 8.7 |
| NONE | 0.0 | 242.5 | 363.6 | 49.9 |
| NONIDET P40 (COMPARATIVE EXAMPLE) | 1.2 | 256.3 | 373.6 | 45.8 |

MxA PROTEIN CONCENTRATION*(ng/mL)

As indicated in Table 1, as compared to when a surfactant is not used (+49.9%) and when Nonidet P40 known to be used in MxA protein measurements (see International Publication No. 2008/053973 pamphlet) is used (+45.8%), it was proven that the measurement variability significantly decreases when a fatty acid alkanolamide is used and that the effect of temperature on the measured values is remarkably suppressed.

Example 2

Examination of the Variation in Measured Values in MxA Protein Measurements—2 (Primary Reaction)

Blood from five MxA protein-positive patients found to have viral infection collected using EDTA.2Na blood collection tubes was used as specimen. Whole blood specimens were diluted 10-fold using a sample diluent to give the samples for measurement.

Primary reactions were performed at 25° C. and 37° C. similarly as in Example 1, except that a specimen diluent containing 1.2% Stafoam DO and a specimen diluent containing 1.2% Nonidet P40 were used as the specimen diluent, and the measurement variation due to reaction temperature was examined. The results are shown in Table 2.

| | | |
|---|---|---|
| Proclin 300 (manufactured by Sigma) | | 0.035% |
| Surfactant | | (type and concentration described in Table 3) |
| 4-AA (manufactured by Saikyo Kasei) | | 0.01% |

The native MxA protein produced in [3] of Example 1 was diluted 20-fold using the specimen diluent in [6] of Example 1 (specifically, Nonidet P40 was used as the "surfactant"), this was left to stand for 30 minutes to solubilize the cells, then this was further diluted eight-fold to give a sample for measurement.

This sample and the standard solutions at each concentration prepared in [6] of Example 1 were used as specimens, and the POD-labeled anti-MxA protein antibody prepared in [5] of Example 1, diluted 800 fold with the above-mentioned POD-labeled antibody dilution buffer was used as the POD-labeled antibody, and measurements were carried out by following the operations described in [7] of Example 1. Specifically, the primary reaction was performed at 25° C., and the secondary reaction was performed at both 25° C. and 37° C.

TABLE 2

| | STAFOAM DO | | | NONIDET P40 | | |
|---|---|---|---|---|---|---|
| WHOLE | MxA PROTEIN CONCENTRATION* | | | MxA PROTEIN CONCENTRATION* | | |
| BLOOD SPECIMEN | REACTION AT 25° C. | REACTION AT 37° C. | MEASUREMENT VARIABILITY (%) | REACTION AT 25° C. | REACTION AT 37° C. | MEASUREMENT VARIABILITY (%) |
| 1 | 29.1 | 29.2 | 0.4 | 25.1 | 27.9 | 11.2 |
| 2 | 17.8 | 18.0 | 1.3 | 12.9 | 14.7 | 13.9 |
| 3 | 26.5 | 27.5 | 3.7 | 26.1 | 28.2 | 8.0 |
| 4 | 8.7 | 9.7 | 12.2 | 8.3 | 10.0 | 20.6 |
| 5 | 15.0 | 16.3 | 8.4 | 8.4 | 10.3 | 22.6 |

MxA PROTEIN CONCENTRATION*(ng/mL)

As shown in Table 2, even when a whole blood specimen is used, the measurement variability is 0% to +12% or less for 1.2% Stafoam DO and, as compared to +8% to 23% of 1.2% Nonidet P40, it was proven that the effect of the reaction temperature on the measured values is remarkably suppressed.

Example 3

Examination of the Variation in Measured Values in MxA Protein Measurements—3 (Secondary Reaction)

POD-labeled antibody dilution buffer having the following composition was prepared.

| | |
|---|---|
| Bis-Tris (manufactured by Dojindo Laboratories) (pH 7.0) | 50 mmol/L |
| BSA (manufactured by InterGen) | 0.1% |

The measurement variabilities of the native MxA protein when reacted at 25° C. and when reacted at 37° C. were calculated by the following equation (I). The results are shown Table 3.

[Equation 2]

$$\text{Variability (\%)} = [(\text{native MxA protein concentration when reacted at 37° C.})/(\text{native MxA protein concentration when reacted at 25° C.}) - 1] * 100 \quad (I)$$

Comparative Example 2

The measurement variability due to the secondary reaction temperature was calculated by a similar method as in Example 3, except that 0.1% Nonidet P40 was used as the surfactant in the POD-labeled antibody dilution buffer of Example 3. The results are shown in Table 3.

TABLE 3

| STRUCTURE | PRODUCT NAME | CONCENTRATION (%) | MxA PROTEIN CONCENTRATION* REACTION AT 25° C. | MxA PROTEIN CONCENTRATION* REACTION AT 37° C. | MEASUREMENT VARIATION (%) |
|---|---|---|---|---|---|
| POE•POP COPOLYMER | PRONON 102 | 0.1 | 385.1 | 352.0 | −8.6 |
|  | PRONON 104 | 0.1 | 372.6 | 369.6 | −0.8 |
|  | EMULGEN PP-230 | 0.1 | 479.7 | 458.5 | −4.4 |
|  | EMULGEN PP-250 | 0.1 | 460.0 | 444.2 | −3.4 |
|  | PRONON 202B | 0.1 | 470.8 | 520.3 | 10.5 |
|  | PRONON 403 | 0.1 | 509.4 | 483.7 | −5.0 |
| POE•POA ALKYL ETHER | UNILUBE 50MB-168 | 0.1 | 345.9 | 329.9 | −4.6 |
|  | UNILUBE 75DE-25 | 0.1 | 313.6 | 258.4 | −17.6 |
|  | UNILUBE 75DE-3800 | 0.1 | 288.3 | 276.7 | −4.0 |
| POE•POP ALKYLPHENYL ETHER | DISPANOL KP189R-40 | 0.1 | 552.5 | 517.7 | −6.3 |
|  | DISPANOL KP189-40 | 0.1 | 560.0 | 493.5 | −11.9 |
| POE POLYCYCLIC PHENYL ETHER | NEWCOL 714 | 0.1 | 535.4 | 465.5 | −13.1 |
|  | NEWCOL 2614 | 0.1 | 551.5 | 464.8 | −15.7 |
| POE•POP POLYCYCLIC PHENYL ETHER | NEWCOL 2616F | 0.1 | 505.8 | 467.7 | −7.5 |
| ETHYLENEDIAMINE POE•POP CONDENSATE | ETHYLENEDIAMINE P040E040 | 0.1 | 534.7 | 520.4 | −2.7 |
| POE ALKYLPHENYL ETHER | NONIDET P40 (COMPARATIVE EXAMPLE) | 0.1 | 532.3 | 381.0 | −28.4 |

MxA PROTEIN CONCENTRATION*(ng/mL)

As indicated in Table 3, it was proven that the measurement variability significantly decreases and that the effect of reaction temperature on the measured values is remarkably suppressed when a POE TOP copolymer, a POE.POP alkyl ether, a POE.POP alkylphenyl ether, a POE polycyclic phenyl ether, a POE.POP polycyclic phenyl ether, or an ethylenediamine POE.POP condensate is used, as compared to when Nonidet P40 is used as the surfactant (−28.4%).

Example 4

Examination of the Variation in Measured Values in MxA Protein Measurements—4 (Secondary Reaction)

Blood from four MxA protein-positive patients found to have viral infection collected using EDTA.2Na blood collection tubes was used as specimen. The whole blood specimens were diluted 10-fold using a sample diluent of [6] of Example 1 (specifically, Nonidet P40 (1.2%) was used as the "surfactant") to give samples for measurement.

The measurement variation due to reaction temperature was examined by carrying out measurements in a similar manner as in Example 3 (specifically, the primary reaction was performed at 25° C., and the secondary reaction was performed at both 25° C. and 37° C.) using POD-labeled antibody dilution buffers containing 0.1% Pronon 403, 0.1% Pronon 102, or 0.1% Nonidet P40, as the surfactant in the POD-labeled antibody dilution buffer of Example 3. The results are shown in Table 4.

TABLE 4

| | POE•POP COPOLYMER | | | POE•POP COPOLYMER | | | POE ALKYLPHENYL ETHER (COMPARATIVE EXAMPLE) | | |
|---|---|---|---|---|---|---|---|---|---|
| | PRONON 403 | | | PRONON 102 | | | NONIDET P40 | | |
| | MxA PROTEIN CONCENTRATION* | | | MxA PROTEIN CONCENTRATION* | | | MxA PROTEIN CONCENTRATION* | | |
| WHOLE BLOOD SPECIMEN | REACTION AT 25° C. | REACTION AT 37° C. | MEASUREMENT VARIABILITY (%) | REACTION AT 25° C. | REACTION AT 37° C. | MEASUREMENT VARIABILITY (%) | REACTION AT 25° C. | REACTION AT 37° C. | MEASUREMENT VARIABILITY (%) |
| 6 | 144.7 | 142.7 | −1.4 | 108.6 | 110.8 | 2.0 | 131.7 | 88.9 | −32.5 |
| 7 | 84.0 | 84.5 | 0.6 | 62.8 | 60.9 | −3.0 | 83.2 | 59.9 | −28.0 |
| 8 | 163.6 | 163.2 | −0.2 | 124.5 | 126.7 | 1.8 | 149.3 | 114.1 | −23.6 |
| 9 | 52.7 | 50.3 | −4.5 | 39.1 | 38.6 | −1.1 | 54.3 | 32.5 | −40.1 |

MxA PROTEIN CONCENTRATION*(ng/mL)

As shown in Table 4, even when a whole blood specimen is used, the measurement variability is −4.5% to +0.6% for Pronon 403 and −3.0% to +2.0% for Pronon 102, and as compared to −40.1% to −23.6% of Nonidet P40, it was proven that the effect of the reaction temperature on the measured values is remarkably suppressed.

Example 5

Examination of the Variation in Measured Values in MxA Protein Measurements—5 (Secondary Reaction)

Blood from five MxA protein-positive patients found to have viral infection collected using EDTA.2Na blood collection tubes was used as specimen. The whole blood specimens were diluted 10-fold using a sample diluent of [6] of Example 1 (specifically, Nonidet P40 (1.2%) was used as the "surfactant") to give samples for measurement.

The measurement variation due to reaction temperature was examined by carrying out measurements in a similar manner as in Example 3 (specifically, the primary reaction was performed at 25° C., and the secondary reaction was performed at both 25° C. and 37° C.) using POD-labeled antibody dilution buffers containing 0.1% Emulgen PP-250, 0.1% Unilube 50 MB-168, 0.1% Dispanol KP189R-40, 0.1% Newcol 2616F, or 0.1% ethylenediamine PO40EO40 as the surfactant in the POD-labeled antibody dilution buffer of Example 3. The results are shown in Table 5.

TABLE 5

| WHOLE BLOOD SPECIMEN | POE•POP COPOLYMER EMULGEN PP-250 | | | POE•POP ALKYL ETHER UNILUBE 50MB-168 | | | POE•POP ALKYLPHENYL ETHER DISPANOL KP189R-40 | | |
|---|---|---|---|---|---|---|---|---|---|
| | MxA PROTEIN CONCENTRATION* | | | MxA PROTEIN CONCENTRATION* | | | MxA PROTEIN CONCENTRATION* | | |
| | REACTION AT 25° C. | REACTION AT 37° C. | MEASUREMENT VARIATION (%) | REACTION AT 25° C. | REACTION AT 37° C. | MEASUREMENT VARIATION (%) | REACTION AT 25° C. | REACTION AT 37° C. | MEASUREMENT VARIATION (%) |
| 10 | 37.7 | 33.6 | −11 | 26.2 | 25.5 | −3 | 40.6 | 35.8 | −12 |
| 11 | 42.8 | 40.1 | −6 | 31.7 | 29.8 | −6 | 45.6 | 40.2 | −12 |
| 12 | 50.1 | 52.1 | 4 | 40.5 | 41.5 | 2 | 54.6 | 52.1 | −5 |
| 13 | 30.3 | 28.3 | −7 | 24.5 | 22.6 | −8 | 33.0 | 28.1 | −15 |
| 14 | 35.3 | 34.8 | −1 | 29.2 | 29.1 | 0 | 37.1 | 34.6 | −6 |

| WHOLE BLOOD SPECIMEN | POE•POP POLYCYCLIC PHENYL ETHER NEWCOL 2616F | | | ETHYLENEDIAMINE POE•POP CONDENSATE ETHYLENEDIAMINE PO40EO40 | | | POE ALKYLPHENYL ETHER (COMPARATIVE EXAMPLE) NONIDET P40 | | |
|---|---|---|---|---|---|---|---|---|---|
| | MxA PROTEIN CONCENTRATION* | | | MxA PROTEIN CONCENTRATION* | | | MxA PROTEIN CONCENTRATION* | | |
| | REACTION AT 25° C. | REACTION AT 37° C. | MEASUREMENT VARIATION (%) | REACTION AT 25° C. | REACTION AT 37° C. | MEASUREMENT VARIATION (%) | REACTION AT 25° C. | REACTION AT 37° C. | MEASUREMENT VARIATION (%) |
| 10 | 40.9 | 33.4 | −18 | 36.1 | 33.5 | −7 | 39.8 | 27.6 | −31 |
| 11 | 46.5 | 37.9 | −19 | 40.7 | 38.3 | −6 | 43.9 | 29.6 | −33 |
| 12 | 54.3 | 50.6 | −7 | 49.4 | 49.0 | −1 | 52.1 | 40.0 | −23 |
| 13 | 33.1 | 27.7 | −16 | 29.7 | 26.2 | −12 | 30.8 | 22.1 | −28 |
| 14 | 38.4 | 34.3 | −11 | 33.9 | 32.5 | −4 | 35.4 | 28.2 | −20 |

MxA PROTEIN CONCENTRATION*(ng/mL)

As shown in Table 5, even when a whole blood specimen is used, the measurement variability is −1% to −11% for Emulgen PP-250, 0% to −8% for Unilube 50 MB-168, −5% to −15% for Dispanol KP189R-40, −7% to −15% for Newcol 2616F, and −1% to −12% for ethylenediamine PO40E040, and as compared to −33% to −20% of Nonidet P40, it was proved that the effect of reaction temperature on the measured values is remarkably suppressed.

Example 6

Kits for measuring MxA protein having components (a) to (g) below were prepared.

(a) Anti-MxA Protein Antibody-Fixed Plate

An anti-MxA protein antibody-fixed plate was prepared by the following method according to the method of Example 1 [4]. First, a 5 μg/mL solution of an anti-MxA protein monoclonal antibody KM1135 in 100 mmol/L phosphate buffer (pH 7.5) containing 100 mmol/L sodium chloride was dispensed in a 96-well microtiter plate (manufactured by Nalge Nunc International) at 100 μL/well, and after allowing the plate to stand for three days, the supernatant was removed by suction. Next, a solution of 1% BlockAce (manufactured by Dainippon Pharmaceutical Co., Ltd.) in 100 mmol/L phosphate buffer (pH 7.5) containing 100 mmol/L sodium chloride was dispensed at 300 μL/well, and blocking was carried out by allowing the plate to stand overnight at room temperature. After removing the blocking solution, the plate was washed using PBS and dried for three days using a vacuum dryer to prepare the anti-MxA protein monoclonal antibody-immobilized plate.

(b) Specimen Diluent

A specimen diluent having the following composition was prepared.

| | |
|---|---|
| Tris (manufactured by Dojindo Laboratories) (pH 8.5) | 0.1 mol/L |
| CHAPS (manufactured by Dojindo Laboratories) | 2.5% |
| Stafoam DO | 1.2% |
| Sodium Chloride | 0.1 mol/L |
| BSA (manufactured by Seikagaku Corporation) | 0.1% |
| Sodium Azide | 0.1% |

(c) POD-Labeled Anti-MxA Protein Antibody Solution

The POD-labeled anti-MxA protein antibody KM1124 prepared by the method of Example 1 [5] was diluted 800-fold using a POD-labeled anti-MxA protein antibody diluent having the following composition to prepare a POD-labeled anti-MxA protein antibody solution.

| | |
|---|---|
| Bis-Tris (manufactured by Dojindo Laboratories) (pH 7.0) | 0.05 mol/L |
| Pronon 202B | 0.1% |
| Sodium Chloride | 50 mmol/L |
| BSA (manufactured by Seikagaku Corporation) | 0.1% |
| 4-AA (manufactured by Saikyo Kasei) | 0.01% |
| Proclin 300 | 0.035% |

(d) Coloring Solution

TMBlue (manufactured by Serological)

(e) Quenching Solution 0.5 mol/L sulfuric acid aqueous solution (f) Washing Solution The following washing solution was prepared.

| | |
|---|---|
| Phosphate buffer (pH 7.2) | 10 mmol/L |
| Tween 20 | 0.05% |
| Sodium Chloride | 0.15 mol/L |

(g) Standard Material and Standard Solutions

The recombinant MxA protein prepared in Example 1 [2] was diluted with phosphate buffer, then freeze-dried to prepare a standard material of the MxA protein.

The prepared standard material in freeze-dried state was diluted using the above-described specimen diluent of (b) to prepare MxA protein solutions at each of the concentrations of 0 (specimen diluent only), 0.375, 0.75, 1.5, 3, 6, 12, and 24 ng/mL, and these solutions were used as standard solutions.

Comparative Example 3

Kits for measuring MxA protein having components (a) to (g) below were prepared.

(a) Anti-MxA Protein Antibody-Fixed Plate

The same anti-MxA protein antibody-fixed plate as in (a) of Example 6.

(b) Specimen Diluent

A specimen diluent having the following composition was prepared.

| | |
|---|---|
| HEPES (manufactured by Dojindo Laboratories) (pH 8.0) | 0.1 mol/L |
| CHAPS (manufactured by Dojindo Laboratories) | 4.9% |
| Nonidet P40 | 1.2% |
| Sodium Chloride | 0.1 mol/L |
| BSA (manufactured by Seikagaku Corporation) | 0.1% |
| Sodium Azide | 0.1% |

(c) POD-Labeled Anti-MxA Protein Antibody Solution

The POD-labeled anti-Mth protein antibody KM1124 prepared by the method of Example 1 [5] was diluted 800-fold using a POD-labeled anti-MxA protein antibody diluent having the following composition to prepare a POD-labeled anti-MxA protein antibody solution.

| | |
|---|---|
| Bis-Tris (manufactured by Dojindo Laboratories) (pH 6.0) | 50 mmol/L |
| Nonidet P40 | 0.1% |
| Sodium Chloride | 50 mmol/L |
| BSA (manufactured by Seikagaku Corporation) | 0.1% |
| 4-AA (manufactured by Saikyo Kasei) | 0.01% |
| Proclin 300 | 0.035% |

(d) Coloring Solution

TMBlue (manufactured by Serological)

(e) Quenching Solution 0.5 mol/L sulfuric acid aqueous solution (f) Washing Solution The following washing solution was prepared.

| | |
|---|---|
| Phosphate buffer (pH 7.2) | 10 mmol/L |
| Tween 20 | 0.05% |
| Sodium Chloride | 0.15 mol/L |

(g) Standard Material and Standard Solutions

The recombinant MxA protein prepared in Example 1 [2] was diluted with phosphate buffer, then freeze-dried to prepare a standard material of the MxA protein.

The prepared standard material in freeze-dried state was diluted using the above-described specimen diluent of (b) to prepare MxA protein solutions at each of the concentrations of 0 (specimen diluent only), 0.375, 0.75, 1.5, 3, 6, 12, and 24 ng/mL, and these solutions were used as standard solutions.

Example 7

The cells prepared in Example 1 [3] were diluted 20-fold using the specimen diluent of Example 6 and left to stand for 30 minutes, then further diluted eight-fold with the specimen diluent to give samples for measurement; the kit of Example 6 was used as the kit; and measurements were carried out by the following procedure.

100 μL of each of the standard solutions prepared in (g) were added to the anti-MxA protein antibody-fixed plate of Example 6 (a) and incubation was carried out for one hour at a given temperature (temperatures of 22° C., 25° C., 28° C., 30° C., or 32° C.) to let the MxA protein bind to the antibody. After removing the reaction solution, the plate was washed five times with 400 μL of the washing solution of (f). Next, 100 μL of the POD-labeled anti-MxA protein antibody solution produced in (c) was added and incubation was carried out for 0.5 hours at a given temperature (temperatures of 22° C., 25° C., 28° C., 30° C., or 32° C.). After the reaction, the reaction solution was removed, and the plate was washed five times with 400 μL of the washing solution of (f). Next, 100 μL of the coloring solution of (d) containing 0.05% tetramethylbenzidine and hydrogen peroxide was added in the dark and incubation was carried out at room temperature for ten minutes, then 100 μL of the quenching solution of (e) was added and incubated at room temperature for 10 minutes to quench the reaction. The absorbance of the reaction solution at 450 nm was measured using a plate reader, and a calibration curve showing the relationship between the MxA protein concentration and the absorbance was produced.

Comparative Example 4

A calibration curve showing the relationship between the MxA protein concentration and the absorbance was prepared by performing the measurements by a method similar as in Example 7, except that the kit of Comparative Example 3 was used instead of the kit of Example 6.

The results of the measurements of Example 7 and Comparative Example 4 are shown in Table 6.

TABLE 6

| KIT | MEASUREMENT METHOD | REACTION TEMPERATURE (° C.) | | | | |
|---|---|---|---|---|---|---|
| | | 22 | 25 | 28 | 30 | 32 |
| EXAMPLE 6 | EXAMPLE 7 | 445.5 (100) | 443.2 (100) | 443.5 (100) | 449.2 (101) | 435.3 (98) |
| COMPARATIVE EXAMPLE 3 | COMPARATIVE EXAMPLE 4 | 381.0 (100) | 360.8 (95) | 338.7 (89) | 297.6 (78) | 284.2 (75) |

The measured values from the reactions at each of the reaction temperatures, and the relative values of the measured values at each temperature as obtained by considering the measured value from the reaction at 22° C. as 100, are both shown in Table 6. A relative value closer to 100 means the measurement is less likely affected by the reaction temperature. As is clear from Table 6, the measured values were remarkably stable in the measurement method of Example 7 which uses the kit of Example 6 containing Stafoam DO (a fatty acid alkanolamide) and Pronon 202B (a POE.POP copolymer) as compared to the measurement method of Comparative Example 4 which uses the kit of Comparative Example 3 containing Nonidet P-40 (a POE alkylphenyl ether). Accordingly, it was proven that the measurement methods of the present invention are methods that are less likely affected by the reaction temperature.

INDUSTRIAL APPLICABILITY

The present invention provides methods and kits for measuring a component to be measured in a specimen, which are useful for diagnosing infections and such.

The invention claimed is:

1. A method for measuring a component, comprising the sequential steps of:
reacting, in the presence of a fatty acid alkanolamide, a component to be measured in a specimen with a first antibody which specifically binds to the component to be measured;
then reacting a labeled second antibody that specifically binds to the component to be measured, to form an immunocomplex comprising the first antibody, the component to be measured, and the labeled second antibody;
thereafter measuring the amount of the label in the formed immunocomplex;
correlating a measured value of the label in the formed immunocomplex with an amount of the component to be measured using a calibration curve; and
determining a concentration of the component to be measured in the specimen,
wherein the specimen comprises cells,
wherein the component is a substance contained within the cells or a protein induced within the cells by cytokines, and
wherein the fatty acid alkanolamide is fatty acid diethanolamide.

2. The method of claim 1, wherein the labeled second antibody is reacted in the presence of a polyoxyethylene nonionic surfactant.

3. A method for measuring a component, comprising the sequential steps of:
reacting a component to be measured in a specimen with a first antibody which specifically binds to the component to be measured;
then reacting, in the presence of a polyoxyethylene nonionic surfactant, a labeled second antibody that specifically binds to the component to be measured, to form an immunocomplex comprising the first antibody, the component to be measured, and the labeled second antibody, the polyoxyethylene nonionic surfactant being selected from the group consisting of polyoxyethylene polyoxypropylene alkyl ether, polyoxyethylene polyoxypropylene alkylphenyl ether, polyoxyethylene polycyclic phenyl ether, polyoxyethylene polyoxypropylene polycyclic phenyl ether, and ethylenediamine polyoxyethylene polyoxypropylene condensate;

thereafter measuring the amount of the label in the formed immunocomplex;

correlating a measured value of the label in the formed immunocomplex with an amount of the component to be measured using a calibration curve; and determining a concentration of the component to be measured in the specimen, wherein the specimen comprises cells, and wherein the component is a substance contained within the cells or a protein induced within the cells by cytokines.

4. The method of claim 2, wherein the polyoxyethylene nonionic surfactant is a polyoxyethylene nonionic surfactant selected from the group consisting of polyoxyethylene polyoxypropylene copolymer, polyoxyethylene polyoxypropylene alkyl ether, and ethylenediamine polyoxyethylene polyoxypropylene condensate.

5. The method of claim 4, wherein a bile acid derivative is added to said specimen and thereafter the component to be measured in the specimen is reacted with the first antibody that binds to the component to be measured.

6. The method of claim 5, wherein the bile acid derivative is a bile acid derivative having zwitterionic surfactant action.

7. The method of claim 6, wherein the bile acid derivative having zwitterionic surfactant action is 3-[(3-cholamidopropyl)dimethylammonio]propanesulfonate or 3-[(3-cholamidopropyl)dimethylammonio]-2-hydroxypropanesulfonate.

8. The method of claim 5, wherein the bile acid derivative is a bile acid derivative having nonionic surfactant action.

9. The method of claim 8, wherein the bile acid derivative having nonionic surfactant action is N,N-bis(3-gluconamidopropyl)cholamide or N,N-bis(3-D-gluconamidopropyl)deoxycholamide.

10. The measurement method of claim 5, wherein the first antibody is immobilized onto an insoluble carrier.

11. The method of claim 10, wherein the specimen is whole blood.

12. The method of claim 11, wherein the component to be measured is MxA protein.

13. A kit for measuring a component in a specimen, comprising:

a first reagent comprising a first antibody which specifically binds to a component to be measured and a fatty acid alkanolamide; and a second reagent comprising a labeled second antibody that specifically binds to the component to be measured, and a polyoxyethylene nonionic surfactant selected from the group consisting of polyoxyethylene polyoxypropylene copolymer, polyoxyethylene polyoxypropylene alkyl ether, polyoxyethylene polyoxypropylene alkylphenyl ether, polyoxyethylene polycyclic phenyl ether, polyoxyethylene polyoxypropylene polycyclic phenyl ether, and ethylenediamine polyoxyethylene polyoxypropylene condensate, wherein the specimen comprises cells, wherein the component is a substance contained within the cells or a protein induced within the cells by cytokines, and wherein the fatty acid alkanolamide is fatty acid diethanolamide.

14. The kit of claim 13, wherein the polyoxyethylene nonionic surfactant is a polyoxyethylene nonionic surfactant selected from the group consisting of polyoxyethylene polyoxypropylene copolymer, polyoxyethylene polyoxypropylene alkyl ether, and ethylenediamine polyoxyethylene polyoxypropylene condensate.

15. The kit of claim 14, wherein the first reagent further comprises a bile acid derivative.

16. The kit of claim 15, wherein the bile acid derivative is a bile acid derivative having zwitterionic surfactant action.

17. The kit of claim 16, wherein the bile acid derivative having zwitterionic surfactant action is 3-[(3-cholamidopropyl)dimethylammonio]propanesulfonate or 3-[(3-cholamidopropyl)dimethylammonio]-2-hydroxypropanesulfonate.

18. The kit of claim 15, wherein the bile acid derivative is a bile acid derivative having nonionic surfactant action.

19. The kit of claim 18, wherein the bile acid derivative having nonionic surfactant action is N,N-bis(3-gluconamidepropyl)cholamide or N,N-bis(3-D-gluconamidepropyl)deoxycholamide.

20. The kit of claim 15, wherein the first antibody is immobilized onto an insoluble carrier.

21. The kit of claim 20, wherein the specimen is whole blood.

22. The kit of claim 21, wherein the component to be measured is MxA protein.

* * * * *